US007858363B2

(12) United States Patent
Jia

(10) Patent No.: US 7,858,363 B2
(45) Date of Patent: Dec. 28, 2010

(54) PLASMID DNA ISOLATION

(75) Inventor: Xiyu Jia, Newport Beach, CA (US)

(73) Assignee: Zymo Research Corporation, Orange, CA (US)

( * ) Notice: Subject to any disclaimer, the term of this patent is extended or adjusted under 35 U.S.C. 154(b) by 0 days.

(21) Appl. No.: 11/490,583

(22) Filed: Jul. 22, 2006

(65) Prior Publication Data

US 2008/0206746 A1 Aug. 28, 2008

(51) Int. Cl.
*C12M 1/00* (2006.01)

(52) U.S. Cl. .................................. 435/283.1; 435/975

(58) Field of Classification Search ........................ None
See application file for complete search history.

(56) References Cited

U.S. PATENT DOCUMENTS

| | | | |
|---|---|---|---|
| 3,677,023 A | 7/1972 | Sun | |
| 5,160,412 A | 11/1992 | Berg | |
| 5,397,711 A * | 3/1995 | Finckh | 436/164 |
| 5,644,035 A | 7/1997 | Koths et al. | |
| 6,277,648 B1 * | 8/2001 | Colpan | 436/177 |
| 2005/0274924 A1 | 12/2005 | Horwath et al. | |
| 2006/0057738 A1 * | 3/2006 | Hall, Jr. | 436/177 |

OTHER PUBLICATIONS

Stratagene ("Gene Characterization Kits" 1988).*
Birnboim and Dolly, A rapid alkaline extraction procedure for screening recombinant plasmid DNA, 1979, N.A.R., V.7 No. 6, 1513-1523, Oxford University Press (England).
Volgelstein and Gillespie, Preparation and analytical purification of DNA from agarose, 1979, P.N.A.S., V. 76, No. 2, 615-619. (USA).
Marko; Chipperfield; and Birnboim, A procedure for the Large-Scale Isolation of Highly Purified Plasmid DNA Using Alkaline . . . 1981, Analytical Biochemistry 121, 382-387 (USA).
.Birnboim, 1983, Methods in Enzymology, V100, 243-255, Aademic Press, Inc. (USA).
Sambrook and Russell, Chapter 1, Protocol 1-3: Preperation of Plasmid DNA by Alkaline Lysis with SDS, 2001, Cold Spring Harbor Laboratory Press, New York, USA.
Sambrook and Russell, Chapter 1, Protocol 9: Purification of Plasmid DNA by Chromatography, 2001, Cold Spring Harbor Laboratory Press, New York, (USA).
Norimichi, T. et al., The Chemistry of Drying an Aqueous Solution of Salts, J. Phys. Chem. A 2009, 113, 12233-12242.

* cited by examiner

*Primary Examiner*—Christopher M. Babic
(74) *Attorney, Agent, or Firm*—Jonathan A Claypool

(57) ABSTRACT

Apparatus, reagents, and methods for isolating plasmid DNA from bacteria by alkaline lysis using a solid or immobilized P2 and/or P3 reagent in combination with a DNA-binding matrix.

16 Claims, 7 Drawing Sheets

| Traditional alkaline lysis | | Embodiment of the invention | |
|---|---|---|---|
| 1. | Transfer bacterial suspension to a tube | 1. | Transfer bacterial suspension to filtration device |
| 2. | Centrifuge to pellet bacteria | 2. | Add P2, mix to lyse the the bacteria |
| 3. | Transfer supernatant to new tube | 3. | Release and mix P3 to neutralize |
| 4. | Resuspend bacteria in P1 | 4. | Centrifuge to filter lysate and to capture DNA |
| 5. | Add P2, mix to lyse bacteria | | |
| 6. | Add P3, mix to neutralize | 5. | Remove/discard flow-through |
| 7. | Centrifuge to separate the the lysate from the precipitation | 6. | Add wash buffer, centrifuge |
| | | 7. | Add elution buffer to the DNA capture device and centrifuge to elute the DNA |
| 8. | Transfer the supernantent/lysate to a DNA-capture device | | |
| 9. | Centrifuge to capture DNA | | |
| 10. | Remove flow through | | |
| 11. | Wash bound DNA, centrifuge | | |
| 12. | Add elution buffer to the DNA-capture device | | |
| 13. | Centrifuge to elute the bound DNA | | |

FIGURE 11

PLASMID DNA ISOLATION

FIELD OF THE INVENTION

The invention relates to methods, apparatus, and reagents for isolating plasmid or similar DNA from bacteria.

BACKGROUND

Plasmid DNA isolation (i.e., plasmid preps, mini-preps, rapid DNA preps, among other procedures) remains a necessary and arduous laboratory task. Plasmid DNA isolation from bacteria has traditionally been performed using the "alkaline lysis" method, in which resuspended bacteria are lysed in NaOH/SDS, neutralized in sodium acetate, and then subjected to centrifugation to remove cell debris (denatured proteins and genomic DNA). Plasmid DNA remains in suspension, ready for further processing (see, e.g., Sambrook and Russel, 2001).

Current popular methods of plasmid DNA preparation are based on the alkaline lysis method followed by separating the flocculent cell debris, including denatured genomic DNA from the plasmid DNA, using a spin-column. The plasmid DNA is typically recovered in a centrifuge tube component of the spin-column, while bacterial debris remains in a lysate filtration device, which is eventually removed and discarded. The recovered DNA must be further transferred and manipulated to remove salts or other contaminants.

While the use of popular spin-column lysate filtration devices has improved the speed and efficiency of plasmid preparation, current methods and apparatus continue to require the separate and sequential addition of the conventional alkaline lysis reagents, i.e., cell pellet resuspension reagent (P1), lysis buffer (P2), and neutralization buffer (P3). Even if bacterial media can be used directly, as in the case of high copy number plasmids, P2 and P3 must still be separately and sequentially added to the cell suspension.

Current methods also require transferring the final cell suspension from a centrifuge tube (or other container in which the bacteria and reagents were combined), to a separate spin-column filtration apparatus, then further transferring and manipulating the filtered lysate to remove contaminants. Current methods are particularly time consuming, tedious, and inefficient (in terms of recovery) when applied to large-scale plasmid DNA preparations.

REFERENCES

Sambrook and Russell (2001) *Molecular Cloning*. Cold Spring Harbor Laboratory Press.

*Remington: The Science and Practice of Pharmacy*—21st Edition. University of the Sciences in Philadelphia (Ed.). (2005) Lippincott Williams & Wilkins.

SUMMARY OF THE INVENTION

The invention provides methods, apparatus, reagents, and kits of parts for isolating plasmid DNA from bacterial cells. In one aspect, the invention provides a method for isolating plasmid DNA from bacteria by alkaline lysis, the method comprising:
  a) providing a bacterial suspension comprising bacteria having plasmid DNA;
  b) incubating the bacterial suspension and a P2 reagent in a mixing chamber; having provided therein a P3 reagent;
  c) releasing the P3 reagent into the bacterial suspension in the mixing chamber to produce an alkaline lysate comprising plasmid DNA;
  d) binding the plasmid DNA to a DNA-binding matrix;
  e) washing the plasmid DNA bound to the DNA-binding matrix;
  f) eluting the plasmid DNA;

wherein, the P2 reagent and/or the P3 reagent is provided in solid or immobilized form in the mixing chamber and is released upon contact with the cell suspension. Depending on the particular embodiment of the invention, the P2 reagent and/or the P3 reagent is provided in solid or immobilized form. Where the P2 reagent is liquid, it may comprise an alcohol such as isopropanol, which allows it to be provided in a more concentrated form. Where the P3 reagent is solid (or in some embodiments where P2 is immobilized) it preferably comprises a solid acid.

In some embodiments of the invention, the mixing chamber is in a lysate filtration device having filtering media for filtering the alkaline lysate prior to binding the plasmid DNA to the DNA-binding matrix. In further embodiments, the lysate filtration device is in fluid contact with a DNA capture device comprising the DNA-binding matrix, wherein lysate filtrate from the lysate filtration device contacts the DNA-binding matrix in the DNA capture device. In a preferred embodiment of the invention, the lysate filtration device and DNA capture device are in a spin-column apparatus. This arrangement allows plasmid DNA to be captured on the DNA-binding matrix follow a single centrifugation step (i.e., a single centrifugation following the release of P3 into the bacterial suspension and formation of the alkaline lysate with characteristic precipitate).

In some embodiments the spin-column is part of a multi-well strip (e.g., an 8-well strip) or is provided in multi-well (e.g., a 24, 48, 96, or 384-well plate) or other high throughput device/format. In other embodiments, a larger lysate filtration device and DNA capture device is used to isolate a greater quantity of plasmid DNA. In yet other embodiments, the DNA-binding matrix is on beads or particles in the mixing chamber.

The invention further includes plasmid DNA produced by the method described herein.

In another aspect, the invention provides a lysate filtration device for filtering a bacterial alkaline lysate. In a particular embodiment, the device comprises a mixing chamber in which a P3 reagent is provided in solid or immobilized form and filtering media in fluid contact with the mixing chamber. A bacterial alkaline lysate is added to the to mixing chamber to contact the solid or immobilized P3 reagent and the resulting neutralized lysate is filtered through the filtering media to remove flocculent bacterial debris.

A further embodiment provides an apparatus comprising a lysate filtration device in fluid contact with a DNA capture device with a DNA-binding matrix. According to this embodiment, filtered lysate from the lysate filtration device contacts the DNA-binding matrix in the DNA capture device. Plasmid DNA in the lysate filtrate binds to the DNA binding matrix.

In a related embodiment of the invention, both P2 and P3 are provided in solid or immobilized form, in which case a bacterial suspension is added directly to the mixing chamber, eliminating the need to separately add P2.

The apparatus may further comprise a sealing cap, wherein the lysate filtration device and sealing cap together form the mixing chamber. The sealing cap may be flexibly attached to the lysate filtration device. In preferred embodiments, the lysate filtration device, or the lysate filtration device and DNA-binding device are a spin-column apparatus.

Where the apparatus comprises a solid or immobilized P3 reagent, the P3 reagent may comprise a solid acid, such as malic acid, maleic acid, citric acid mono-sodium or disodium salts, or other acids or acidic salts which dissolve in an aqueous solution to produce a pH of less than 7.0. The solid or immobilized P3 reagent may be disposed anywhere in the mixing chamber, including in the sealing cap, which together with the lysate filtration device create the mixing chamber. In particular embodiments, a solid P3 reagent is provided under or a behind a water-soluble protective barrier or film, which dissolves upon contact with the cell suspension (which should at this point include a P2 reagent dissolved in the bacterial suspension).

The invention further provides modified P2 and P3 reagents optimized for use with the methods and apparatus of the invention.

In particular embodiments of the invention, a pH-sensitive dye is present in the mixing chamber, the bacterial suspension, or in a P2 or P3 reagent to allow the end user to monitor the pH of the bacterial suspension during lysis and neutralization. In this manner, the end user observes a color change as P3 dissolves into a lysed bacterial suspension comprising P2.

The invention further provides modified alkaline lysis reagents. One aspect of the invention is a modified P2 reagent comprising alcohol, in addition to SDS and NaOH (or other alkali metal hydroxide), to reduce SDS precipitation. In preferred embodiments, the alcohol is selected from isopropanol, 1-propanol, and ethanol. Another aspect of the invention is a modified P3 reagent comprising a solid acid. In preferred embodiments, the modified P3 reagent is provided in solid or immobilized form.

The invention further includes kits of parts comprising an apparatus and/or reagents of the invention.

BRIEF DESCRIPTION OF THE DRAWINGS

FIG. 11: Flowchart comparing the conventional method of alkaline lysis with a spin-column embodiment of the invention.

DETAILED DESCRIPTION OF THE INVENTION

This invention provides methods, apparatus and reagents for rapidly isolating plasmid and similar epimeric forms of DNA from bacteria.

In one embodiment, the invention utilizes a lysate filtration device for filtering precipitated material (i.e., proteins and genomic DNA complexes) from a bacterial alkaline lysate prepared directly from a bacterial culture, without first performing the separate procedures of concentrating the bacteria, denaturing the plasmid and bacterial genomic DNA using a strong base, and then neutralizing the resulting solution with acid. These separate steps are conventionally performing using three aqueous solutions, i.e., resuspension buffer, lysis buffer, and neutralization buffer, often abbreviated P1, P2, and P3, respectively.

An important feature of the present invention is that the lysate filtration device comprises at least one solid or immobilized alkaline lysis reagent (i.e., P2 and/or P3), which dissolves or is released upon contact with a bacterial suspension. The lysate filtration device comprising such a solid or immobilized alkaline lysis reagent is preferably linked to a capture device comprising a DNA-binding matrix for binding plasmid DNA present in the filtered lysate from the lysate filtration device. In this manner, the apparatus and method of the invention allows plasmid DNA to be isolated in a single spin-column apparatus using a single centrifugation step. The plasmid DNA is then eluted from the DNA-capture device ready to use.

This invention improves on current apparatus and methods in several ways:

It allows the use of a bacterial culture/suspension directly, i.e., there is no need to centrifuge or filter the bacterial culture to concentrate the bacteria or to remove the culture medium. P1 is no longer required.

It uses at least one solid or immobilized alkaline lysis reagent provided in the lysate filtration device, eliminating to the need to add an equivalent liquid reagent.

It is readily adapted to capture plasmid DNA from a bacterial suspension following a single centrifugation event.

It provides modified P2 and P3 reagents, which are optimized for use with the apparatus and method.

A. The Lysate Filtration Column Device and Method for use

Figure 1:
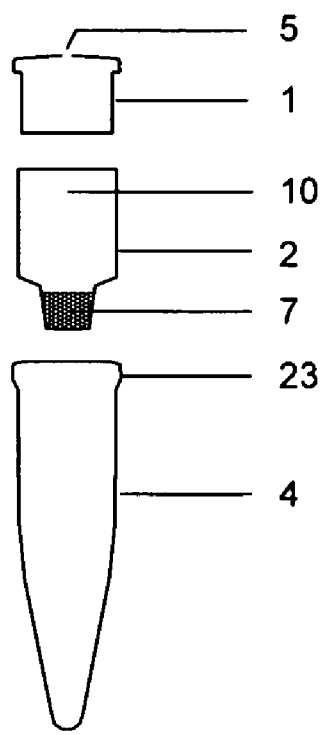
FIG. 1: Drawing depicting a spin-column embodiment of the invention.

The invention is best understood with the aid of the accompanying Figures. Referring to FIG. 1, the invention provides a lysate filtration apparatus based on a spin-column. The apparatus comprises a lysate filtration device 2 in which filtering media (a filter) 7 is disposed and a sealing cap 1 to reduce spillage from the resulting interior space, herein referred to as the mixing chamber 10. The mixing chamber is the combination of the enclosed volume of the filtering device 2 and the enclosed volume of the cap 1, either of which volumes can readily be adjusted to accommodate solid or immobilized P2 and P3 reagents. A centrifuge tube 4 is provided to collect lysate filtrate following centrifugation.

A non-air-tight sealing cap provides sufficient venting during centrifugation and fluid movement through the filter 7. Alternatively, an air vent 5 may be provided. The centrifuge tube 4 may be a generic laboratory item, such as a 1.5 ml microfuge tube. In preferred embodiments, the centrifuge tube has a lip 23, which prevents it from falling to the bottom of the rotor (not shown). In embodiments described below, a DNA capture device 3 for binding (i.e., capturing) plasmid DNA in the lysate filtrate is interposed between the lysate filtration device 2 and centrifuge tube 4 (see, e.g., FIG. 7).

Figure 2:
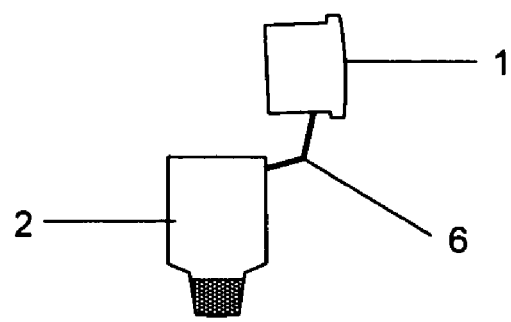
FIG. 2: Drawing depicting an embodiment of the sealing cap.
Figure 8:
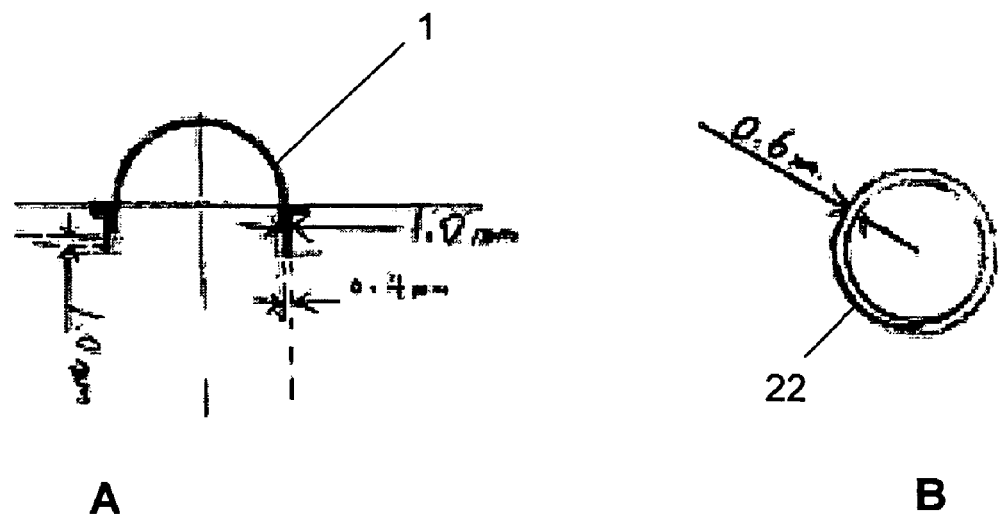
FIG. 8: Drawing depicting a preferred embodiment of the sealing cap having a groove (shown in A) to accept an internal ring (B) for retaining a water-soluble film (not shown).

The lysate filtration device 2 and the sealing cap 1 may be a single assembly or separate components that come together at a sealing surface (not shown) to produce a mixing chamber 10 suitable for containing a cell suspension. The sealing cap 1 and lysate filtration device 2 may be attached via a flexible hinge 6, as shown in FIG. 2. The sealing cap 1 may have a substantial volume to contain a P2 or P3, or other reagent or to increase the volume of the mixing chamber 10. A preferred embodiment of the sealing cap is shown in FIG. 8 (dimensions in mm). The ring 22 shown in FIG. 8B fits into the groove on the bottom (open end) of the cap 1 (FIG. 8A) for holding in place a circular sheet of water-soluble film for immobilizing a P2 or P3 reagent. Examples of suitable films are provided herein.

An important feature of the invention is that the bacterial culture/suspension is introduced into the mixing chamber 10 to contact first P2, then P3, and then is subjected to centrifugation to filter the lysate and capture the plasmid DNA, all without the further introduction of liquid into the mixing chamber.

Figure 3:
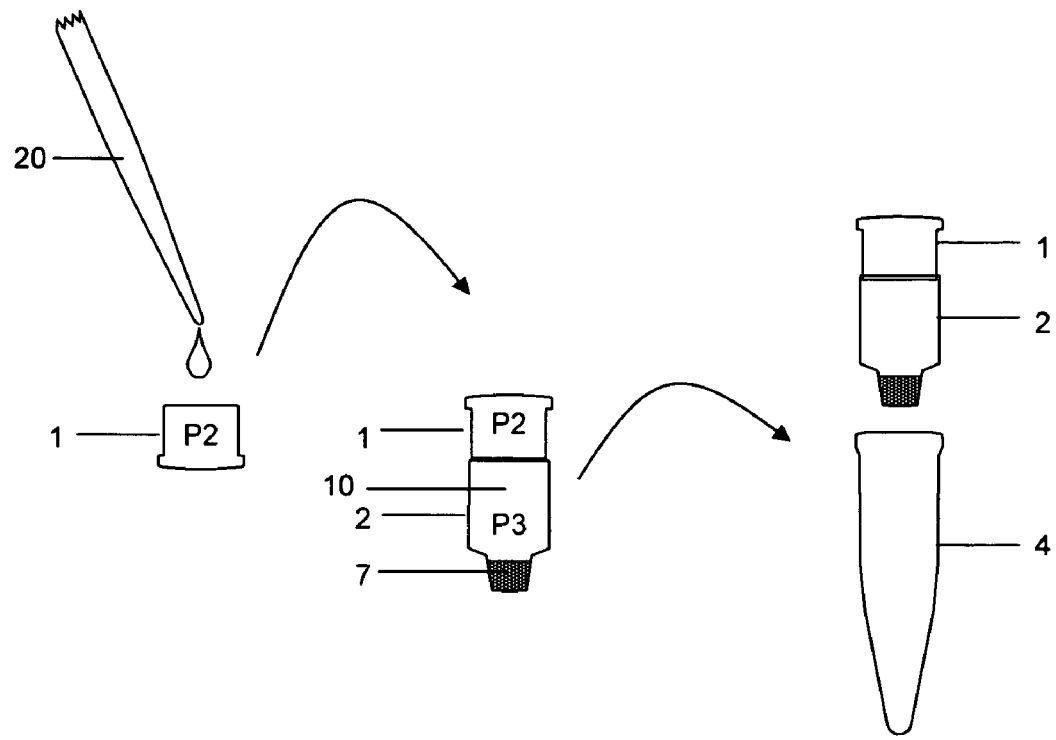
FIG. 3: Diagram depicting an embodiment of the invention in which P2 is provided in the sealing cap and P3 is provided in the lysate filtration device.

In some embodiments of the invention, the bacterial suspension is introduced (e.g., using a pipeting device 20) to the sealing cap 1, in which P2 is provided (FIG. 3). Following incubation, the sealing cap 1 is closed on the lysate filtration device 2 comprising P3, creating a mixing chamber 10. The contents of the mixing chamber 10 can be mixed by inversion or other means, so long as the sealing cap 1 remains closed on the filter device 2 and the bacterial suspension remains confined.

Figure 4:
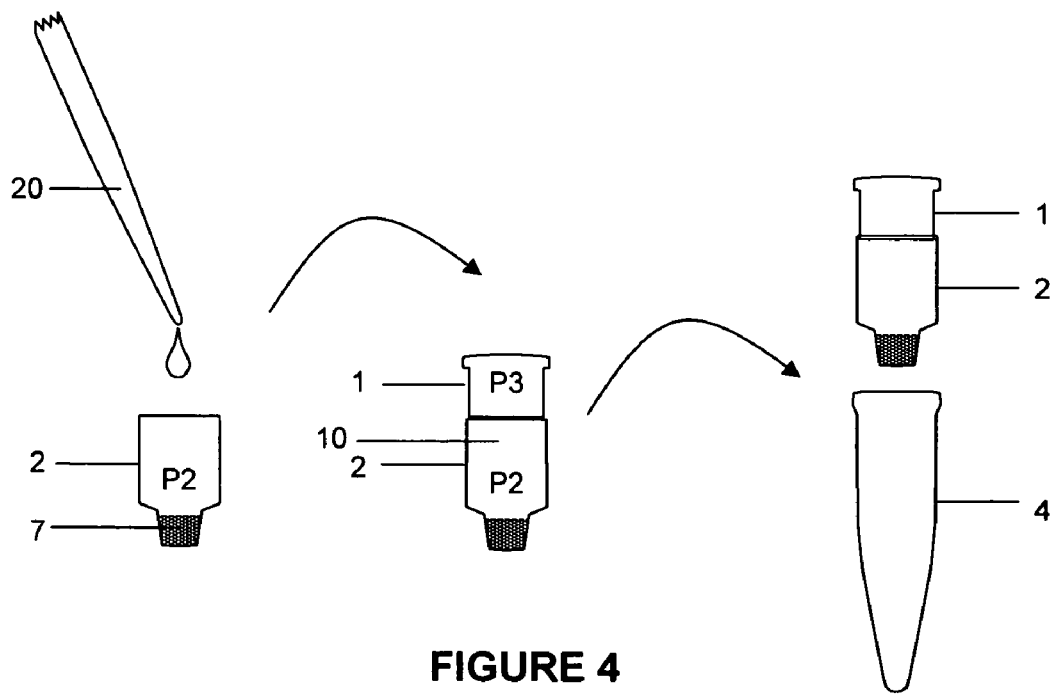
FIG. 4: Diagram depicting an embodiment of the invention in which P2 is provided in the lysate filtration device and P3 is provided in the sealing cap.

In another embodiment of the invention, P2 is provided in the lysate filtration device 2 and P3 is provided in the sealing cap 1 (FIG. 4). In such embodiments, bacterial suspensions are added to the filtration unit 2 to dissolve the solid or immobilized P2. After a few seconds of incubation, the sealing cap 1, in which P3 is disposed, is closed and the contents of the mixing chamber 10 are mixed.

Figure 5:
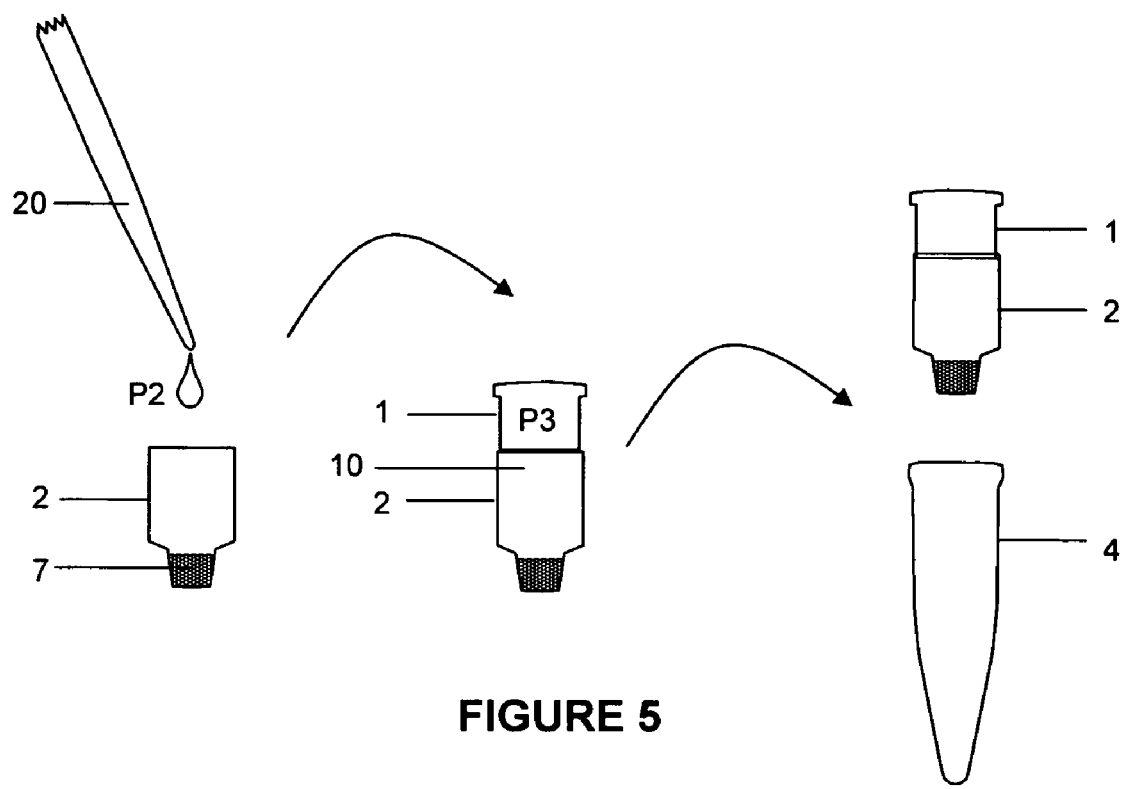
FIG. 5: Diagram depicting an embodiment of the invention in which P2 is provided in liquid form and P3 is provided in the sealing cap.

In another embodiment of the invention, P2 or P3 is provided as a solid or immobilized form and the other reagent is provided as a liquid. In a preferred embodiment of the invention, P3 is provided as a solid or immobilized form in the mixing chamber, as illustrated in FIG. 5. According to this embodiment, a cell suspension is combined with liquid P2, and the resulting mixture is added to solid or immobilized P3. Alternatively, the cell suspension and P2 are separately added to the mixing chamber 10, in either order. P3 may be provided in the sealing cap 1 (as shown in FIG. 5) or in the lysate filtration device 2. P2 should be well mixed with the bacterial suspension before the suspension contacts P3.

Solid and immobilized forms of P2 and P3 reagents include solid (e.g., dry crystal or powder forms) or semi-solid forms (e.g., formulations comprising binders, gums, gels, dissolving matrices, and the like). The solid or semi-solid P2 or P3 reagents are immobilized (i.e., restricted, confined, or localized to a portion of the mixing chamber) by virtue of their solid or semi-solid form and/or immobilized in or behind water-soluble films, barriers, or packages and/or physical barriers.

Following incubation in a P2 and a P3 reagent, the alkaline lysate is subjected to centrifugation and the lysate filtrate comprising plasmid DNA is collected. The plasmid DNA recovered is sufficiently pure for most applications, but may be further processed to improve purity. Additional processing includes but is not limited to treatment with a chaotropic agent treatment and alcohol (e.g., ethanol, isopropanol, and/or butanol) precipitation followed by binding the DNA to a solid matrix (e.g., glass fibers or beads) to remove any contaminants. The washed DNA is typically eluted in water or an aqueous buffer.

B. Plasmid Preparation Column Apparatus and Method for use

Figure 7:
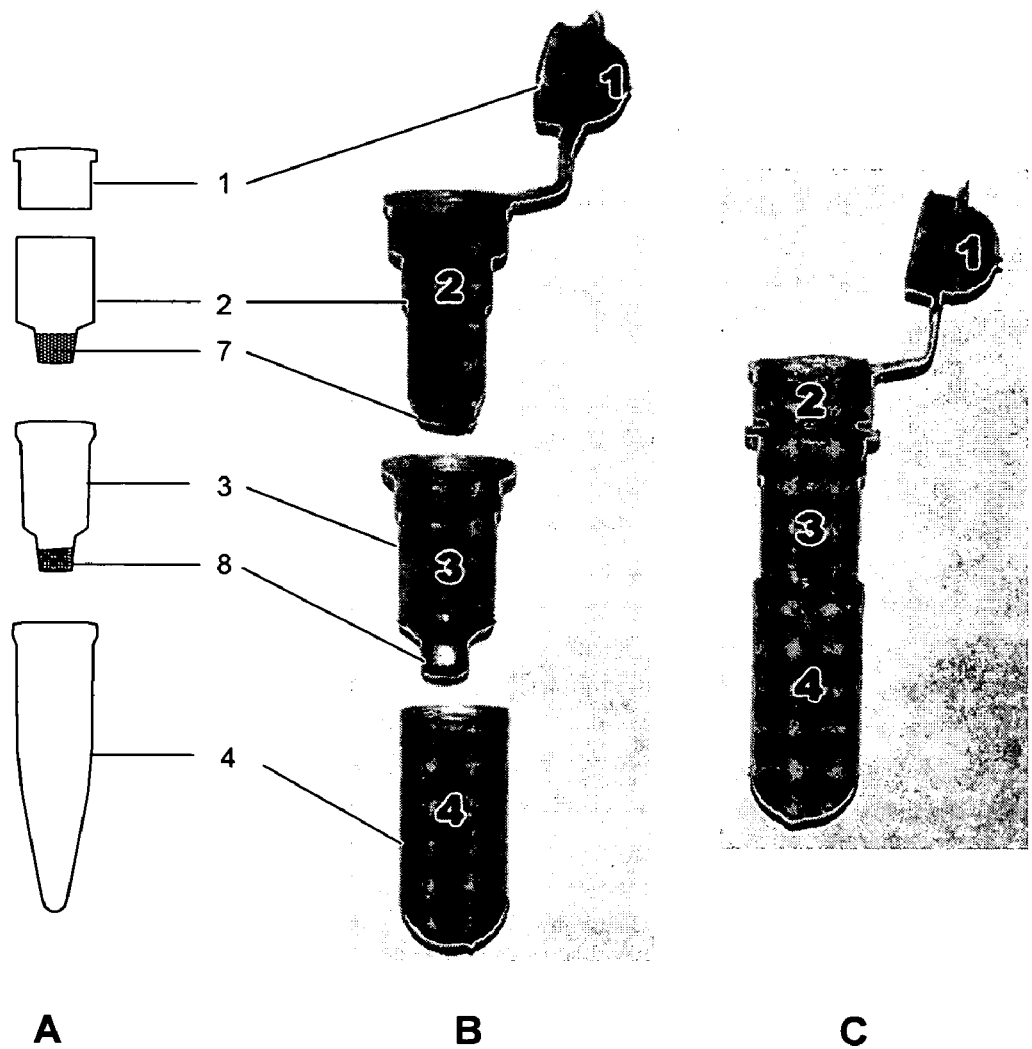
FIG. 7: Diagram and photograph depicting a spin-column embodiment of the invention. The sealing cap, lysate filtration device, DNA capture device, and centrifuge tube are numbered in the photograph.

In preferred embodiments of the method and apparatus, a spin-column lysate filtration device 2 is combined with a DNA capture device 3 to produce a single-centrifugation-step-plasmid DNA isolation apparatus. An example of this embodiment of the invention is shown in FIG. 7. A DNA capture device 3 having a DNA-binding material/matrix (e.g., a DNA-binding filter) 8, such as a silicon matrix (e.g., WHATMAN: type C and F glass fibers), is interposed between the lysate filtration device 2 and the centrifuge tube 4. Alkaline lysis is performed as before. However, upon centrifugation, the lysate filtrate passes through the DNA-capture device 3. Plasmid DNA binds to the DNA-binding filter 8 in the DNA-capture device 3, while the depleted lysate filtrate passes through to the centrifuge tube 4.

The plasmid DNA is washed/rinsed on the DNA-binding filter 8 using, e.g., an ethanol-containing wash solution such as 75% ethanol with 5 mM Tris-HCl, pH 7.4. In preferred embodiments, the DNA-capture device is adapted to fit in or on a centrifuge tube and in or on a vacuum manifold to facilitate washing/rinsing and elution. In other embodiments the device may be adapted for use with an 8-well strip, 24, 48, 96, or 384-well plates, or other high throughput devices or formats. The bound plasmid DNA is eluted in a small volume of aqueous solution, such as water or TE and may be used without further purification.

Figure 9:
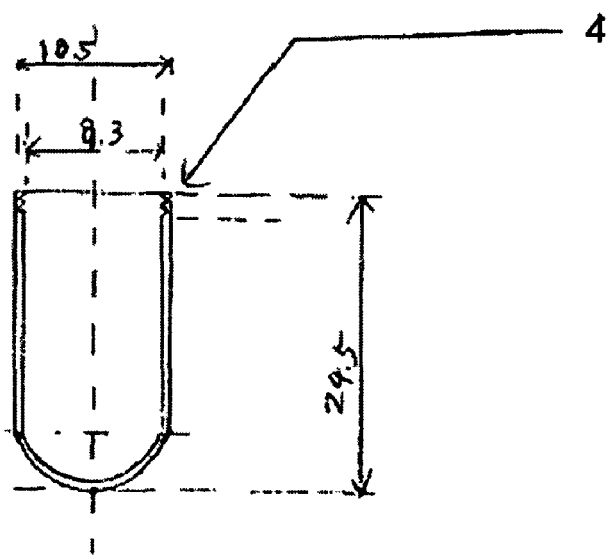
FIG. 9: Drawing depicting a preferred embodiment of the centrifuge tube for use with the device shown in FIG. 7.
Figure 10:
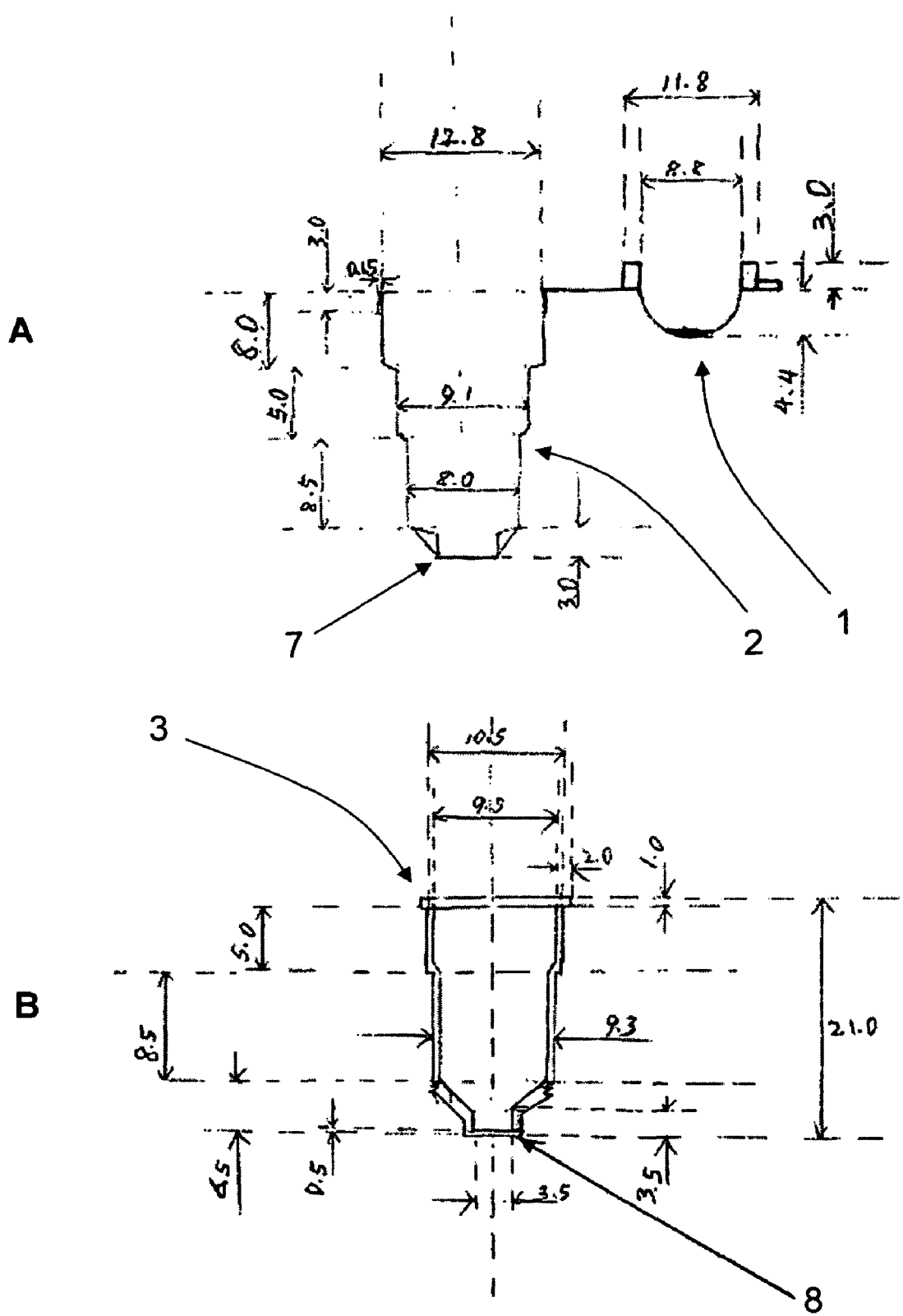
FIG. 10: Drawing depicting a preferred embodiment of the lysate filtration device (A) and DNA capture device (B) shown in FIG. 7.

In this embodiment, it is desirable to use a centrifuge tube 4 that lacks a lip 23 as shown in FIG. 1. This allows the assembled apparatus (FIG. 7C) to be positioned lower in the rotor to avoid interferences with the rotor cap or centrifuge lid. Drawings of a prototype lysate filtration device 2 and a prototype DNA-capture device 3 are shown in FIGS. 10A and 10B, respectively (dimensions in mm). A drawing of a preferred centrifuge tube 4 is shown in FIG. 9 (dimensions in mm). The centrifuge tube 4 contacts the bottom of the centrifuge rotor (i.e., bottoms-out in the rotor), such that the centrifuge tube 4 does not separate from the DNA-capture device during centrifugation. In some embodiments, the centrifuge tube 4 snaps or screws onto the DNA-capture device 3, such that the components of the apparatus do not separate in the rotor upon centrifugation. This later arrangement also facilitates the removal of the intact apparatus (FIG. 7C) from the centrifuge.

In some embodiments of the invention, a pH-sensitive colored indicator is provided in the lysate filtration device, mixed with P2 and/or P3, or added to the cell suspension. The colored indicator allows the user to visualize the pH of the cell suspension in the mixing chamber, allowing the user to monitor the lysis and neutralization steps. For example, where phenol red is used as an indicator, the cell suspension is red after adding P2 but turns yellow upon neutralization with P3. In this manner, the end user can monitor the progress of the alkaline lysis procedure and determine when complete lysis and neutralization has occurred. RNase A may also be separately added to the cell suspension or provided in P2 or P3. In a particular embodiment, dry RNase A is mixed with P3 solid. The time and manner of addition of RNase A is not critical.

A comparison of the steps required for using an apparatus and method of the invention (particularly using the embodiment shown in FIG. 5 along with the DNA-capture device shown in FIG. 7) with the prior art is shown in FIG. 11. One skilled in the art will recognize the significant saving of time and effort using the invention.

C. Bead Method and Apparatus

Figure 6:
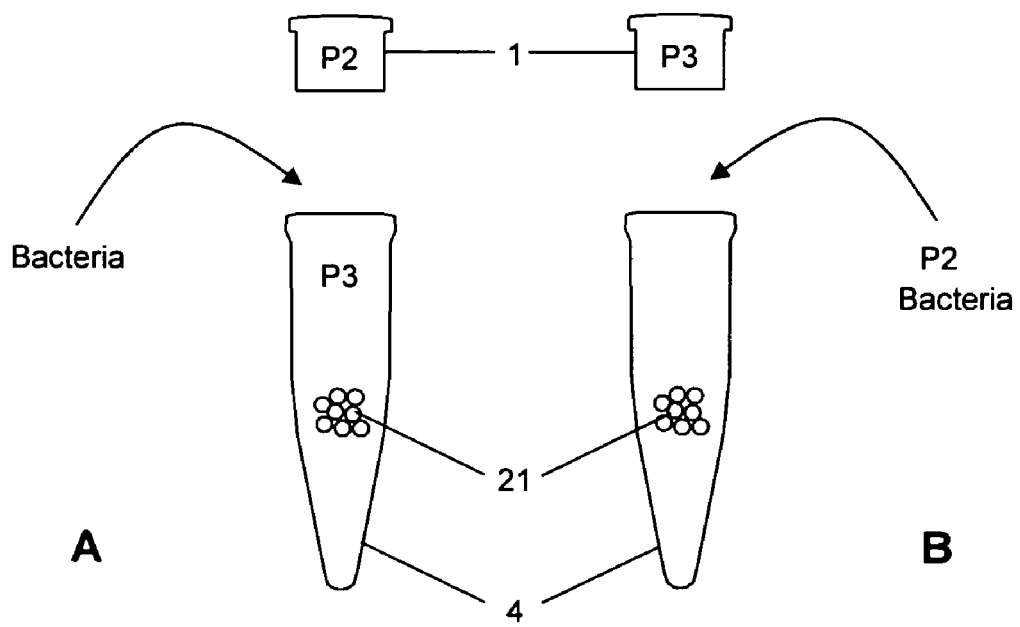
FIG. 6: Diagram depicting bead embodiments of the invention.

In another embodiment of the invention, solid or immobilized P2 and/or P3 reagents are used in combination with a DNA-binding matrix provided by beads or other convenient-to-handle particles. This embodiment is exemplified in FIG. 6.

According to this embodiment, a bacterial suspension (A) or a bacterial suspension with P2 added (B) is introduced into the mixing chamber created by a centrifuge tube 4 and a cap 1. After mixing the contents to release P2 and/or P3, plasmid DNA from lysed bacteria binds to the beads 21. The bead are washed or rinsed, e.g., using an ethanol-containing solution, and the DNA is eluted from the beads. Beads are separated from contaminants and wash buffer by centrifugation, filtration, or in the case of magnetic beads, use of a magnet. DNA is then eluted from the beads using water or an aqueous buffer.

The beads 21 may be provided in the mixing chamber 10 along with P3. For example, the beads could be combined with the solid or immobilized P3, as described above and as shown in, e.g., FIGS. 3 and 4. Alternatively, the beads can be separately added to the cell suspension, added with P2, or otherwise provided in the mixing chamber to bind plasmid DNA from lysed bacteria. The time of addition of the beads is not critical, provided that they are present to bind plasmid DNA in the alkaline lysate. In a preferred embodiment, the beads 21 and solid or immobilized P3 are present in the centrifuge tube 4 (or cap 1) to which a bacterial suspension mixed with P2 is added.

In a related embodiment, DNA-binding beads 21 are used in combination with a lysate filtration device 2. According to this embodiment, filtered lysate from the lysate filtration device 2 is incubated in the presence of beads 21 rather than the DNA-binding matrix 8 present in a DNA capture device 3. Bound plasmid DNA is washed and eluted as above.

D. Modified P2 Reagent

Conventional P2 reagents contain NaOH and SDS and may be used in either liquid or dry form, depending on the embodiment of the invention. Both NaOH and SDS are supplied and stored as dry chemicals. In embodiments of the invention wherein P2 is a liquid, it is desirable to minimize the volume of P2 to permit the use of a greater volume of bacterial suspension. Reducing P2 volume also facilitates handling and storage of the solution. Because conventional P2 is already a concentrated solution, significantly reducing the volume leads to precipitation.

A feature of the invention is the preferential use of modified P2 comprising NaOH (or other metal hydroxide), SDS, and isopropanol. Isopropanol reduces precipitation and allows P2 to be provided as a more concentrated liquid (i.e., in less volume). EDTA may be added to P2 to assist in membrane lysis of the bacteria. A particular embodiment of modified P2 reagent is 0.8 M NaOH, 5% SDS, 5 mM EDTA, and 7% isopropanol. These amounts are not critical. 1-10% isopropanol is sufficient to reduce precipitation. Examples of suitable amounts include 1, 2, 3, 5, 7, and 10%. Even quantities of about 15 or 20% do not adversely affect plasmid recovery. Similar alcohols, such as 1-propanol and ethanol, may replace isopropanol.

For the same amount of cell suspension, less volume of modified P2 is required compared to conventional P2. For example, while conventional mini-preps use about equal volumes of P1 and P2 solutions; a sufficient amount of modified P2 can be provided in only about ⅛ the volume of the suspended cells (e.g., about 800 μl cells and about 100 μl modified P2). Note that these ratios/volumes are examples and are not to be construed as limiting.

E. Modified P3 Reagent

While conventional liquid P3 may be used with some embodiments of the invention, it is not readily provided in solid or immobilized form because it comprises acetic acid, which is a liquid a room temperature. This invention provides a modified P3 reagent, which is readily provided in solid form. The modified P3 reagent comprises a solid acid, a chaotropic agent, and potassium chloride or sodium iodide. Preferred solid acids are malic acid and citric acid; however, other acids (malonic, maleic, succinic, tartaric, pyruvic, and similar acids) are expected to work in the invention. Preferred chaotropic agents include guanidinium-HCl, guanidinium isothiocyanate, iodide, perchlorate, and trichloroacetate. Other potassium salts, such as potassium acetate, can replace KCl. As noted elsewhere, RNase A may be added to P3, to the cell suspension, to P2, or added at any convenient time, preferably prior to capturing the DNA with the DNA binding matrix 8 or other solid matrix, e.g., beads 22.

A particular modified P3 dry mix formulation is 16.2 g KCl, 3.09 g malic acid, 16.5 g guanidine-HCl, and 2 mg RNase A. These values and ratios are approximate and not critical. Other modified P3 reagent formulation will work with the invention.

F. Solid or Immobilized Reagents

An important feature of the invention is the use of a solid or immobilized reagent in place of an aqueous reagent. One skilled in the art will recognize that solid in this case refers to dry solid or semi-solid compositions and formulations that would serve to immobilize the P2 and/or P3 reagent(s) for several months at room temperature. The solid reagents should be stable under typical room temperature storage conditions. High viscosity liquid formulations of P2 and/or P3 may also be used to practice the invention, provided that P2 and/or P3 remains substantially immobilized within the lysate filtration device.

Methods for coating surfaces with dry compositions are well known in the art, and include drying (e.g., spray-drying and freeze-drying) the P2 and/or P3 compositions on the inside surface of the mixing chamber in the lysate filtration device and/or sealing cap. Dry reagents may also be provided as tablets. A binder, adhesive, or other additive may be used, so long as the formulation does not interfere with the alkaline lysis process or recovery of plasmid DNA (see e.g., Remington, 2005). Formulations should be water-soluble to dissolve in the cell suspension.

Dry or formulated chemicals can be also be provided in a water-soluble package or provided under or a behind a water-soluble protective barrier or film. As used herein, water-soluble polymers include polymers that are technically "sensitive to the presence of water," rather than water-soluble. Useful films include polyethylene/vinyl alcohol although other films are known in the art and include (but are not limited to) polyacrylate, polyurethane, and other polyesters hydrogels, polylactides, ethylene vinyl acetate, ethylene vinyl alcohol, poly-D-(−)-3-hydroxybutyric acid, degradable lactic acid-glycolic acid copolymers, copolymers of L-glutamic acid and gamma ethyl-L-glutamate, poly (2-hydroxyethyl-methacrylate), crosslinked polyethers including cross-linked poly(ethylene oxide), carboxymethylcellulose, hydrocolloid type materials, cellulose acetate, and phthalate.

Dry chemicals can also be suspended or dispersed in a water-soluble, semi-solid admixture (e.g., a paste, gum, grease, or similar form), so long as the underlying carrier or polymer does not interfere with the alkaline lysis process or recovery of the plasmid DNA. Ideally, the formulation should be of sufficient character and viscosity to immobilize the P2 and/or P3 reagent to facilitate storage and handling prior to addition of the cell suspension (typically by the end user).

In embodiments where both P2 and P3 are provided in solid or immobilized form, the P2 reagent should dissolve before the P3 reagent. In particular, the P2 formulation should dissolve upon contact with a cell suspension, while the P3 formulation should dissolve several seconds (e.g., 30, 60 or more) after the P2 formulation has been released, dissolved, and dispersed sufficiently to lyse the bacteria.

These times are exemplary and are not to be construed as limiting. Shorter delays, e.g., for automated processing, or longer delays, e.g., to provide additional time for mixing and handling, may be preferable to the end-user.

Other methods and techniques for depositing dry or semi-solid chemical compositions are known in the art and are not part of the principle invention. The reader should give the terms solid and immobilized form their broadest interpretation.

G. Definitions

Scientific terms have generally been given their ordinary meaning as used in the art. The following inventions are provided for clarity:

Plasmids: Plasmids are (typically) circular double-stranded DNA molecules distinct from the bacterial chromosomal DNA and capable of autonomous replication. Plasmid DNA is often called vector DNA. As used herein, plasmid DNA includes all epimeric forms of DNA that can be propagated in bacteria (e.g., plasmids, phagemids, cosmids, shuttle vectors, and the like).

Alkaline lysate: A bacterial suspension following treatment with P2 and P3. Plasmid DNA in an alkaline lysate has been denatured and renatured.

Bacterial suspension: Bacteria in media, lysis buffer (i.e. P1), water, or another liquid reagent that does not interfere with the steps of alkaline lysis. The bacterial suspension may be directly from a culture or may be the result of centrifugation and resuspension of bacteria from a culture, plate, stab, slant, contaminated water specimen, biological warfare specimen, or other sample comprising or suspected of comprising bacteria having plasmid DNA Binding the plasmid DNA to the DNA-binding matrix: Incubating a solution or suspension comprising plasmid DNA (e.g. an alkaline lysate) in the presence of DNA binding matrix, such as a silica-based matrix, such that plasmid DNA binds to the DNA-binding matrix. A chaotropic agent, such as sodium iodide or guanidinium-HCl is usually present to increase binding efficiency. The plasmid DNA may then be eluted from the DNA-binding matrix using an aqueous solution, such as water or Tris-acetate buffer (TE). As used herein, the expression binding the plasmid DNA to the DNA-binding matrix is synonymous with capturing the plasmid DNA.

Combined with: Mixed, added in addition to, added together with, added as part of a bulk mixture to, or otherwise brought together.

Contact the DNA-binding matrix: To physically contact a DNA-binding matrix, as when a liquid, such as an alkaline lysis lysate comprising or suspected of comprising plasmid DNA, is passed over a DNA binding matrix in a column or incubated in the presence of DNA binding matrix on beads or another solid matrix.

Filtering media: A matrix suitable for trapping insoluble particle present in an alkaline lysate, including paper filters, cheesecloth, and similar bulk filter materials used to make column frits. Many materials may be used to practice the invention but cost, consistency, and stability should be considered.

Fluid contact: Arranged so as to allow fluid to flow from one device to another as described herein and as understood in the art. Fluid contact is synonymous with the phrase fluid communication.

Films: Flexible films are typically planar forms of plastics, which should be thick enough to support and retain a solid or immobilized composition. Films include single layer polymers and multilayer structures. Water-soluble films may include tie layers and copolymers. Films should be soluble in P2 and/or P3 buffer as appropriate. Release times can be tailored by polymer selection and film thickness. Examples of materials suitable for use with the invention include but are not limited to polyacrylate, polyurethane, and other polyesters hydrogels, polylactides, ethylene vinyl acetate, ethylene vinyl alcohol (EVOH, including ethylene vinyl alcohol copolymers), vinyl acetate, poly-D-(−)-3-hydroxybutyric acid, degradable lactic acid-glycolic acid copolymers, copolymers of L-glutamic acid and gamma ethyl-L-glutamate, poly (2-hydroxyethyl-methacrylate), crosslinked polyethers including cross-linked poly(ethylene oxide), carboxymethylcellulose, and hydrocolloid type materials.

Isolate plasmid DNA: To remove bacterial debris, salts, and other contaminants, to an extent sufficient to permit the use of the plasmid DNA in standard laboratory DNA manipulations and assays, such as sequence analysis, PCR analysis, methylation analysis, etc. The quality of the plasmid DNA isolated using the methods, apparatus, and reagents described herein is similar to that obtained using conventional alkaline lysis coupled to spin-column methods.

Lysate filtrate: A bacterial suspension following treatment with P2 and P3 and subsequent filtration to remove genomic DNA and aggregated bacteria proteins. Lysate filtrate comprises plasmid DNA unless it has been in contact with a DNA-binding matrix, in which case it is depleted of plasmid DNA.

Provided in: Positioned, placed, presented, disposed, stored, sequestered, isolated, contained, or made available in. This expression is used with reference to P2 and/or P3 reagents, which are provided in the mixing chamber (including the lysate filtration device and the sealing cap) where they contact a bacterial suspension according to the methods of the invention. The P2 and/or P3 reagents may be provided in solid or immobilized form (as described, herein), or in liquid form, depending on the particular embodiment of the invention.

Single centrifugation step: Requiring no more than one centrifugation event at an appropriate speed, i.e., a single acceleration and deceleration cycle or one "spin" in a centrifuge.

Solid or immobilized: Solid refers to a P2 and/or P3 reagent that is provided in solid or semi-solid form. Solid forms include granules, crystals, powders, chalks, and other solid forms. Semi-solid forms include pastes, creams, gels, ointments, colloidal suspensions, and like compositions. The solid and semi-solid forms may include any number or binders or additives, provided that they do not interfere with the process of alkaline lysis or plasmid DNA-binding to the solid matrix. Examples of binders and additives are found in Remington (2005). Immobilized refers to a P2 and/or P3 reagent that remains substantially confined or localized to a portion of the mixing chamber until it dissolves in a bacterial suspension (including a bacterial suspension to which P2, RNase, dye, or other component. has been added). Unless otherwise indicated by context, solid or immobilized means solid and/or immobilized. By contrast, a liquid P2 or P3 reagent, as used in conventional methods of plasmid DNA preparation, is neither solid, nor immobilized.

Solid and semi-solid P2 and/or P3 reagents may be immobilized in the lysate filtration device or in the sealing cap, depending on the embodiment of the invention. Solid reagents may be immobilized by being dried (including freeze and spray-dried) onto a surface in the mixing chamber. Solid forms may be applied to a surface in the mixing chamber using an adhesive that does not interfere with the methods of the invention. Semi-solid forms may be immobilized by virtue of their tendency to adherence to surfaces, in which case they are spread, injected, dropped, or otherwise applied to a surface in the mixing chamber. Semi-solid formulations may be heated or diluted in a solvent prior to their application.

Solid or semi-solid P2 and/or P3 reagents may be immobilized in or behind water-soluble films, barriers, or packages. As used herein, the term water-soluble encompasses films that are, technically, sensitivity to water, or otherwise dissolve in an aqueous bacterial suspension in a manner that is chemically distinct but functionally equivalent to water-solubility. Films maybe used to cover a solid or semi-solid P2 or P3 reagent, in which case the edges and or corners or a sheet of film are glued or mechanically attached such that the P2 or P3 reagent is substantially immobilized or localized at a predetermined portion of the mixing chamber. Films may also be used to package (i.e., wrap, envelope, encase, or enclose) solid or semi-solid reagents, in which cases the packages may be placed in the lysate filtration device or sealing cap.

Solid or semi-solid P2 and/or P3 reagents may also be immobilized behind insoluble or physical barriers (e.g., sieves, gratings, perforations, or restrictor plates, or similar restraints.), so long as the P2 or P3 reagents are substantially immobilized or localized in the mixing chamber and are in fluid contact with the bacterial suspension so as to facilitate dissolution and thorough mixing of the reagent(s) in/with the bacterial suspension. Physical barriers can be combined with soluble barriers, e.g., to permit the use of a thinner or less robust film.

Solid acid: An acid that is solid at room temperature. A solid acid can be an acidic salt. Examples include malic, malonic, maleic, succinic, tartaric, citric, pyruvic acid, mono or disodium citric acid, and similar compounds. These acids are distinguishable from acetic acid, which is a liquid a room temperature. Preferred solid acids are stable for many months at room temperature, inexpensive, non-hygroscopic, and readily available. Other examples of solid acids are described in Remington (2005).

Spin-column apparatus: Columns for use in standard centrifuges, microfuges, vacuum-manifolds, or low or high-pressure (HPLC, HPCE) systems, all of which are known in the art. A single column means an individual chromatographic column, for example a discrete spin-column, vacuum column, gravity-flow column. Multi-well formats may also be used, wherein each well operates as a single column. The column preferably includes a narrow, tapered neck where filter material (in the case of the lysate filtration device) or, e.g., a silica resin material (or matrix; in the case of the DNA-capture device) is contained. A tapered neck in combination with a small amount of DNA-binding material facilitates efficient elution and recovery of plasmid DNA.

Substantially confined or localized to: Confined or localized sufficiently so as not to interfere with alkaline lysis and plasmid DNA recovery according to the particular embodiment of the invention. Solid or immobilized P2 and/or P3 reagents should remain in a predetermined portion of the mixing chamber throughout shipping and storage, until the end user adds bacterial suspension; however, minor leakage, migration, or contamination or reagents (e.g., less than about 2% or even less than 5%) is unlikely to interfere with the methods and apparatus described herein.

H. Utility

As plasmid DNA preparation remains a necessary and important laboratory procedure, the present invention is of readily apparent value to researchers and technicians. The apparatus and methods of the invention will allow the rapid and efficient screening of large numbers of plasmids (e.g., from transformed bacteria). In addition to saving time and effort, the apparatus and methods of the invention will allow researchers to identify rare or infrequent plasmids, such as those resulting from complicated cloning schemes, those comprising toxic genes subject to deletion and rearrangement, and those harboring nucleotide sequence that are under-represented in a population (e.g., a population of PCR products).

The invention may be especially useful for field workers, who have limited access to laboratory supplies and equipment or require a rapid method and apparatus for isolating plasmid or similar DNA. Field workers include epidemiologists, virologists, and medical personal. Military specialists could also benefit from use of devices and methods of the present invention.

The invention is well suited to be supplied in a kit form with associated parts, which would preferably include a column or bead embodiment of the invention, along with appropriate reagents and instructions for use. In particular kits for use in the field are contemplated that would further facilitate isolation of DNA from samples and organisms at source locations. These include labile samples not amenable to transport or laboratory culture. Kits of parts for performing the methods of the invention are particularly useful for identifying plasmid-carrying bacteria in hospitals (including military and other field hospitals), at sites of natural disasters, terrorist attacks, and other catastrophic events, in contaminated water and food supplies, in patient and/or corpse biopsy or pathological samples (e.g., blood, feces, urine, sputum, seminal and vaginal fluids, or other bodily fluids). Kits may also be used to identify biological warfare agents comprising bacteria (e.g., the anthrax bacillus) that harbor plasmid-borne determinants of pathogenesis.

The embodiments of the invention described herein are merely exemplary and should not be construed as limiting. One skilled in the art will appreciate additional embodiments and modifications upon reading the disclosure.

The invention claimed is:

1. A lysate filtration device for filtering a bacterial alkaline lysate, the device comprising a mixing chamber, having a top and bottom opening, a P3 reagent provided in the mixing chamber as a dry formulation, a filtering media positioned in the mixing chamber, the filtering media being separate from the P3 reagent and in fluid contact with the mixing chamber, the mixing chamber being configured to receive a bacterial alkaline lysate through the top opening, wherein contact between the P3 reagent and the bacterial alkaline lysate can occur, whereby contact between the P3 reagent and the bacterial alkaline lysate will result in a neutralized lysate, the neutralized lysate further comprising a flocculent bacterial debris and a remaining bacterial lysate, and wherein the filtering media is for filtering the flocculent bacterial debris, from the remaining bacterial lysate.

2. An apparatus comprising the lysate filtration device of claim 1 in fluid contact with a DNA capture device, the DNA capture device having a DNA-binding matrix provided in the DNA capture device, wherein filtered lysate from the lysate filtration device can contact the DNA-binding matrix in the DNA capture device, and wherein plasmid DNA in the lysate filtrate can bind to the DNA binding matrix.

3. The apparatus of claim 2, further comprising a sealing cap, and wherein the lysate filtration device and sealing cap together form the mixing chamber.

4. The apparatus of claim 3, further comprising the P3 reagent disposed in the sealing cap.

5. The apparatus of claim 3 further comprising the P3 reagent disposed under or behind a water-soluble protective barrier or film; wherein the water-soluble protective barrier is positioned to dissolve upon contact with a cell suspension.

6. The apparatus of claim 1, wherein the apparatus is a spin-column apparatus.

7. The apparatus of claim 6, wherein the apparatus is in multi-well format.

8. A kit comprising the apparatus of claim 6.

9. A kit comprising the apparatus of claim 7.

10. The apparatus of claim 3 wherein the lysate filtration device and the DNA capture device are linked.

11. The apparatus of claim 10 wherein the linked device forms one mixing chamber.

12. A lysate filtration device for filtering a bacterial alkaline lysate, the device comprising a mixing chamber, having a top and bottom opening, a P2 and a P3 and reagent provided in the mixing chamber, the P2 and P3 reagents being disposed as dry formulations, wherein the P2 media is disposed to contact a cell suspension and dissolve before the P3 reagent, a filtering media positioned in the mixing chamber, the filtering media being separate from the P2 and P3 reagents, wherein the filtering media is in fluid contact with the mixing chamber, the mixing chamber being configured to receive a bacterial cell suspension through the top opening, whereby contact between the bacterial cell suspension and the P2 and P3 reagents can occur, and whereby contact between the bacterial cell suspension, the P2 reagent and the P3 reagent will result in a bacterial alkaline lysate that is rapidly neutralized, the neutralized lysate further comprising a flocculent bacterial debris and a remaining bacterial lysate, and wherein the filtering media is for filtering the flocculent bacterial debris, from the remaining bacterial lysate.

13. The apparatus of claim 2, wherein the dry formulation P3 reagent is selected from the group consisting of tablets, powders, granules, crystals, chalks, films, and polymers.

14. The apparatus of claim 2, wherein the dry formulation P3 further comprises a potassium salt, a chaotropic agent, and a solid acid.

15. The apparatus of claim 14, wherein the solid acid is selected from the group consisting of malic acid, citric acid, malonic acid, maleic acid, succinic acid, tartaric acid, and pyruvic acid.

16. The apparatus of claim 14, wherein the chaotropic agent is selected from the group consisting of guanidinium-HCl, iodide, perchlorate, and trichloroacetate.

* * * * *